(12) United States Patent
Ginn (10) Patent No.: US 7,740,640 B2
(45) Date of Patent: Jun. 22, 2010

(54) CLIP APPARATUS FOR CLOSING SEPTAL DEFECTS AND METHODS OF USE

(75) Inventor: Richard S. Ginn, San Jose, CA (US)

(73) Assignee: Ovalis, Inc., Mountain View, CA (US)

( * ) Notice: Subject to any disclaimer, the term of this patent is extended or adjusted under 35 U.S.C. 154(b) by 1237 days.

(21) Appl. No.: 10/856,493

(22) Filed: May 28, 2004

(65) Prior Publication Data

US 2004/0249398 A1 Dec. 9, 2004

Related U.S. Application Data (63) Continuation of application No. 09/948,502, filed on Sep. 6, 2001, now Pat. No. 6,776,784.

(51) Int. Cl.
*A61B 17/03* (2006.01)
(52) U.S. Cl. .................. 606/142; 606/151; 606/213
(58) Field of Classification Search ............... 606/213, 606/216, 219, 221, 151, 157, 142
See application file for complete search history.

(56) References Cited

U.S. PATENT DOCUMENTS

| 2,670,673 A | 3/1954 | Gordon et al. |
| 3,874,388 A | 4/1975 | King et al. |
| 3,875,648 A | 4/1975 | Bone |
| 4,006,747 A | 2/1977 | Kronenthal et al. |
| 4,007,743 A | 2/1977 | Blake |
| 4,316,469 A | 2/1982 | Kapitanov |
| 4,576,162 A | 3/1986 | McCorkle |
| 4,601,718 A | 7/1986 | Possis et al. |
| 4,665,906 A | 5/1987 | Jervis |

(Continued)

FOREIGN PATENT DOCUMENTS

EP   0 432 320 A1   6/1991

(Continued)

OTHER PUBLICATIONS

Ruiz, et al., The Puncture Technique: A New Method for Transcatheter Closure of Patent Foramen Ovale, Catheterization and Cardiovascular Interventions 53:369-372 (2001).

(Continued)

*Primary Examiner*—Anhtuan T Nguyen
*Assistant Examiner*—Ryan J Severson
(74) *Attorney, Agent, or Firm*—Orrick, Herrington & Sutcliffe LLP (57) ABSTRACT

A device for closing a septal defect, such as a patent foramen ovale, includes a clip formed from a superelastic material that is inserted into a septum wall of a heart. The clip is advanced through a patient's vasculature, e.g., within a delivery apparatus, until the clip is disposed within a first chamber adjacent the septal defect. Tines of the clip are directed through a flap of tissue of the septal defect until the tines of the clip are disposed within a second opposing chamber. The clip then transforms into its relaxed state, wherein the tines of the clip engage with a surface of the second chamber, thereby substantially closing the septal opening.

100 Claims, 5 Drawing Sheets

U.S. PATENT DOCUMENTS

| | | |
|---|---|---|
| 4,669,473 A | 6/1987 | Richards et al. |
| 4,696,300 A | 9/1987 | Anderson |
| 4,702,250 A | 10/1987 | Ovil et al. |
| 4,705,040 A | 11/1987 | Mueller et al. |
| 4,721,115 A | 1/1988 | Owens |
| 4,741,336 A | 5/1988 | Failla et al. |
| 4,779,616 A | 10/1988 | Johnson |
| 4,800,890 A | 1/1989 | Cramer |
| 4,802,478 A | 2/1989 | Powell |
| 4,836,204 A | 6/1989 | Landymore et al. |
| 4,850,960 A | 7/1989 | Grayzel |
| 4,861,336 A | 8/1989 | Helzel |
| 4,878,893 A | 11/1989 | Chin |
| 4,892,098 A | 1/1990 | Sauer |
| 4,902,508 A | 2/1990 | Badylak et al. |
| 4,917,089 A | 4/1990 | Sideris |
| 4,929,246 A | 5/1990 | Sinofsky |
| 4,985,014 A | 1/1991 | Orejola |
| 4,994,069 A | 2/1991 | Ritchart et al. |
| 5,021,059 A | 6/1991 | Kensey et al. |
| 5,037,433 A | 8/1991 | Wilk et al. |
| 5,041,129 A | 8/1991 | Hayhurst et al. |
| 5,049,153 A | 9/1991 | Nakao et al. |
| 5,067,957 A | 11/1991 | Jervis |
| 5,073,166 A | 12/1991 | Parks et al. |
| 5,108,420 A | 4/1992 | Marks |
| 5,112,310 A | 5/1992 | Grobe |
| 5,171,218 A | 12/1992 | Fonger et al. |
| 5,171,259 A | 12/1992 | Inoue |
| 5,190,050 A | 3/1993 | Nitzsche |
| 5,190,528 A | 3/1993 | Fonger et al. |
| 5,190,546 A | 3/1993 | Jervis |
| 5,192,301 A | 3/1993 | Kamiya et al. |
| 5,219,358 A | 6/1993 | Bendel et al. |
| 5,222,974 A | 6/1993 | Kensey et al. |
| 5,236,440 A | 8/1993 | Hlavacek |
| 5,242,427 A | 9/1993 | Bilweis |
| 5,250,054 A | 10/1993 | Li |
| 5,250,055 A | 10/1993 | Moore et al. |
| 5,257,637 A | 11/1993 | El Gazayerli |
| 5,281,234 A | 1/1994 | Wilk et al. |
| 5,282,827 A | 2/1994 | Kensey et al. |
| 5,284,488 A | 2/1994 | Sideris |
| 5,290,272 A | 3/1994 | Burstein et al. |
| 5,290,278 A | 3/1994 | Anderson |
| 5,300,065 A | 4/1994 | Anderson |
| 5,304,184 A | 4/1994 | Hathaway et al. |
| 5,304,185 A | 4/1994 | Taylor |
| 5,312,341 A | 5/1994 | Turi |
| 5,312,435 A | 5/1994 | Nash et al. |
| 5,318,525 A | 6/1994 | West et al. |
| 5,330,488 A | 7/1994 | Goldrath |
| 5,330,496 A | 7/1994 | Alferness |
| 5,334,191 A | 8/1994 | Poppas et al. |
| 5,334,217 A | 8/1994 | Das |
| 5,357,979 A | 10/1994 | Imran |
| 5,364,410 A | 11/1994 | Failla et al. |
| 5,370,679 A | 12/1994 | Atlee, III |
| 5,383,852 A | 1/1995 | Stevens-Wright |
| 5,387,227 A | 2/1995 | Grice |
| 5,394,880 A | 3/1995 | Atlee, III |
| 5,403,329 A | 4/1995 | Hinchcliffe |
| 5,403,338 A | 4/1995 | Milo |
| 5,409,469 A | 4/1995 | Schaerf |
| 5,409,481 A | 4/1995 | Poppas et al. |
| 5,413,584 A | 5/1995 | Schulze |
| 5,417,699 A | 5/1995 | Klein et al. |
| 5,417,713 A | 5/1995 | Cohen |
| 5,421,338 A | 6/1995 | Crowley et al. |
| 5,425,744 A | 6/1995 | Fagan et al. |
| 5,431,696 A | 7/1995 | Atlee, III |
| 5,433,727 A | 7/1995 | Sideris |
| 5,441,504 A | 8/1995 | Pohndorf et al. |
| 5,443,478 A | 8/1995 | Purdy |
| 5,451,235 A | 9/1995 | Lock et al. |
| 5,461,235 A | 10/1995 | Cottrell et al. |
| 5,462,560 A | 10/1995 | Stevens |
| 5,462,561 A | 10/1995 | Vode |
| 5,474,573 A | 12/1995 | Hatcher |
| 5,478,353 A | 12/1995 | Yoon |
| 5,486,183 A | 1/1996 | Middleman et al. |
| 5,486,193 A | 1/1996 | Bourne et al. |
| 5,503,634 A | 4/1996 | Christy |
| 5,507,744 A | 4/1996 | Tay et al. |
| 5,507,811 A | 4/1996 | Koike et al. |
| 5,522,873 A | 6/1996 | Jackman et al. |
| 5,527,388 A | 6/1996 | Berke et al. |
| 5,545,138 A | 8/1996 | Fugoso et al. |
| 5,548,872 A | 8/1996 | Oetiker |
| 5,554,162 A | 9/1996 | DeLange |
| 5,570,671 A | 11/1996 | Hickey |
| 5,573,540 A | 11/1996 | Yoon |
| 5,573,542 A | 11/1996 | Stevens |
| 5,575,772 A | 11/1996 | Lennox |
| 5,577,299 A | 11/1996 | Thompson et al. |
| 5,578,045 A | 11/1996 | Das |
| 5,582,616 A | 12/1996 | Bolduc et al. |
| 5,584,803 A | 12/1996 | Stevens et al. |
| 5,601,571 A | 2/1997 | Moss |
| 5,618,311 A | 4/1997 | Gryskiewicz |
| 5,620,461 A | 4/1997 | Muijs Van De Moer et al. |
| 5,626,599 A | 5/1997 | Bourne et al. |
| 5,634,936 A | 6/1997 | Linden et al. |
| 5,645,557 A | 7/1997 | Yoon |
| 5,649,950 A | 7/1997 | Bourne et al. |
| 5,658,280 A | 8/1997 | Issa |
| 5,662,643 A | 9/1997 | Kung et al. |
| 5,682,906 A | 11/1997 | Sterman et al. |
| 5,702,368 A | 12/1997 | Stevens et al. |
| 5,702,421 A | 12/1997 | Schneidt |
| 5,709,224 A | 1/1998 | Behl et al. |
| 5,709,707 A | 1/1998 | Lock et al. |
| 5,713,867 A | 2/1998 | Morris |
| 5,713,911 A | 2/1998 | Racenet |
| 5,714,297 A | 2/1998 | Chamberlain et al. |
| 5,716,367 A | 2/1998 | Koike et al. |
| 5,720,754 A | 2/1998 | Middleman et al. |
| 5,722,981 A | 3/1998 | Stevens |
| 5,725,512 A | 3/1998 | Swartz et al. |
| 5,725,552 A | 3/1998 | Kotula et al. |
| 5,725,554 A | 3/1998 | Simon et al. |
| 5,728,151 A | 3/1998 | Garrison et al. |
| 5,733,294 A | 3/1998 | Forber et al. |
| 5,738,652 A | 4/1998 | Boyd et al. |
| 5,741,429 A | 4/1998 | Donadio, III et al. |
| 5,759,170 A | 6/1998 | Peters |
| 5,769,812 A | 6/1998 | Stevens et al. |
| 5,772,672 A | 6/1998 | Toy et al. |
| 5,776,162 A | 7/1998 | Kleshinski |
| 5,782,860 A | 7/1998 | Epstein et al. |
| 5,792,094 A | 8/1998 | Stevens et al. |
| 5,797,960 A * | 8/1998 | Stevens et al. ............... 606/213 |
| 5,807,339 A | 9/1998 | Bostrom et al. |
| 5,810,882 A | 9/1998 | Bolduc et al. |
| 5,810,884 A | 9/1998 | Kiim |
| 5,814,016 A | 9/1998 | Valley et al. |
| 5,814,068 A | 9/1998 | Koike et al. |
| 5,814,097 A | 9/1998 | Sterman et al. |
| 5,823,956 A | 10/1998 | Roth et al. |
| 5,827,216 A | 10/1998 | Igo et al. |
| 5,829,447 A | 11/1998 | Stevens et al. |
| 5,836,311 A | 11/1998 | Borst et al. |
| 5,853,422 A * | 12/1998 | Huebsch et al. ............... 606/213 |
| 5,855,614 A | 1/1999 | Stevens et al. |

| | | | |
|---|---|---|---|
| 5,861,003 A | 1/1999 | Latson et al. | |
| 5,865,791 A | 2/1999 | Whayne et al. | |
| 5,868,702 A | 2/1999 | Stevens et al. | |
| 5,868,733 A | 2/1999 | Ockuly et al. | |
| 5,868,753 A | 2/1999 | Schatz | |
| 5,879,366 A | 3/1999 | Shaw et al. | |
| 5,879,499 A | 3/1999 | Corvi | |
| 5,885,238 A | 3/1999 | Stevens et al. | |
| 5,893,856 A | 4/1999 | Jacob et al. | |
| 5,895,404 A | 4/1999 | Ruiz | |
| 5,902,319 A | 5/1999 | Daley | |
| 5,904,703 A | 5/1999 | Gilson | |
| 5,908,428 A | 6/1999 | Scirica et al. | |
| 5,910,150 A | 6/1999 | Saadat | |
| 5,911,717 A | 6/1999 | Jacobsen et al. | |
| 5,913,810 A | 6/1999 | Andre | |
| 5,913,842 A | 6/1999 | Boyd et al. | |
| 5,919,200 A | 7/1999 | Stambaugh et al. | |
| 5,924,424 A | 7/1999 | Stevens et al. | |
| 5,927,284 A | 7/1999 | Borst et al. | |
| 5,928,181 A | 7/1999 | Coleman et al. | |
| 5,928,250 A | 7/1999 | Koike et al. | |
| 5,931,848 A | 8/1999 | Saadat | |
| 5,941,899 A | 8/1999 | Granger et al. | |
| 5,944,738 A | 8/1999 | Amplatz et al. | |
| 5,947,997 A | 9/1999 | Pavcnik et al. | |
| 5,955,110 A | 9/1999 | Patel et al. | |
| 5,967,977 A | 10/1999 | Mullis et al. | |
| 5,972,013 A | 10/1999 | Schmidt | |
| 5,976,174 A | 11/1999 | Ruiz | |
| 5,980,503 A | 11/1999 | Chin | |
| 5,989,268 A | 11/1999 | Pugsley, Jr. et al. | |
| 5,993,475 A | 11/1999 | Lin et al. | |
| 6,007,563 A | 12/1999 | Nash et al. | |
| 6,010,517 A | 1/2000 | Baccaro | |
| 6,013,052 A | 1/2000 | Durman et al. | |
| 6,015,378 A | 1/2000 | Borst et al. | |
| 6,015,417 A | 1/2000 | Reynolds, Jr. | |
| 6,024,756 A | 2/2000 | Huebsch et al. | |
| 6,027,476 A | 2/2000 | Sterman et al. | |
| 6,030,007 A | 2/2000 | Bassily et al. | |
| 6,036,699 A | 3/2000 | Andreas et al. | |
| 6,036,720 A | 3/2000 | Abrams et al. | |
| 6,056,760 A | 5/2000 | Koike et al. | |
| 6,071,271 A | 6/2000 | Baker et al. | |
| 6,071,292 A * | 6/2000 | Makower et al. | 606/158 |
| 6,077,281 A | 6/2000 | Das | |
| 6,077,291 A | 6/2000 | Das | |
| 6,080,182 A | 6/2000 | Shaw et al. | |
| 6,090,084 A | 7/2000 | Hassett et al. | |
| 6,090,096 A | 7/2000 | St. Goar et al. | |
| 6,093,199 A | 7/2000 | Brown et al. | |
| 6,095,997 A | 8/2000 | French et al. | |
| 6,110,145 A | 8/2000 | Macoviak | |
| 6,113,609 A | 9/2000 | Adams | |
| 6,113,610 A | 9/2000 | Poncet | |
| 6,113,611 A | 9/2000 | Allen et al. | |
| 6,117,145 A | 9/2000 | Wood et al. | |
| 6,117,159 A | 9/2000 | Huebsch et al. | |
| 6,126,658 A | 10/2000 | Baker | |
| 6,127,410 A | 10/2000 | Duhaylongsod | |
| 6,132,438 A | 10/2000 | Fleischman et al. | |
| 6,135,981 A | 10/2000 | Dyke | |
| 6,142,975 A | 11/2000 | Jalisi et al. | |
| 6,149,664 A | 11/2000 | Kurz | |
| 6,152,141 A | 11/2000 | Stevens et al. | |
| 6,152,144 A | 11/2000 | Lesh et al. | |
| 6,162,195 A | 12/2000 | Igo et al. | |
| 6,162,202 A | 12/2000 | Sicurelli et al. | |
| 6,165,183 A | 12/2000 | Kuehn et al. | |
| 6,165,204 A | 12/2000 | Levinson et al. | |
| 6,171,329 B1 | 1/2001 | Shaw et al. | |
| 6,171,338 B1 | 1/2001 | Talja et al. | |
| 6,174,322 B1 | 1/2001 | Schneidt | |
| 6,179,809 B1 | 1/2001 | Khairkhahan et al. | |
| 6,187,039 B1 | 2/2001 | Hiles et al. | |
| 6,200,313 B1 | 3/2001 | Abe et al. | |
| 6,206,895 B1 | 3/2001 | Levinson | |
| 6,206,907 B1 | 3/2001 | Marino et al. | |
| 6,214,029 B1 | 4/2001 | Thill et al. | |
| 6,221,092 B1 | 4/2001 | Koike et al. | |
| 6,231,561 B1 | 5/2001 | Frazier et al. | |
| 6,245,080 B1 | 6/2001 | Levinson | |
| 6,254,550 B1 | 7/2001 | McNamara et al. | |
| 6,270,490 B1 | 8/2001 | Hahnen | |
| 6,270,515 B1 | 8/2001 | Linden et al. | |
| 6,275,730 B1 | 8/2001 | KenKnight et al. | |
| 6,277,138 B1 | 8/2001 | Levinson et al. | |
| 6,277,139 B1 | 8/2001 | Levinson et al. | |
| 6,280,432 B1 | 8/2001 | Turovskiy et al. | |
| 6,280,460 B1 | 8/2001 | Bolduc et al. | |
| 6,287,317 B1 | 9/2001 | Makower et al. | |
| 6,290,674 B1 | 9/2001 | Roue et al. | |
| 6,293,920 B1 | 9/2001 | Sweezer et al. | |
| 6,302,903 B1 | 10/2001 | Mulier et al. | |
| 6,305,378 B1 | 10/2001 | Lesh | |
| 6,306,150 B1 | 10/2001 | Levinson | |
| 6,306,424 B1 | 10/2001 | Vyakarnam et al. | |
| 6,308,090 B1 | 10/2001 | Tu et al. | |
| 6,309,415 B1 | 10/2001 | Pulnev et al. | |
| 6,312,446 B1 | 11/2001 | Huebsch et al. | |
| 6,319,263 B1 | 11/2001 | Levinson | |
| 6,322,548 B1 | 11/2001 | Payne et al. | |
| 6,328,727 B1 | 12/2001 | Frazier et al. | |
| 6,336,898 B1 | 1/2002 | Borst et al. | |
| 6,342,064 B1 | 1/2002 | Koike et al. | |
| 6,346,074 B1 | 2/2002 | Roth | |
| 6,346,099 B1 | 2/2002 | Altman | |
| 6,346,112 B2 | 2/2002 | Adams | |
| 6,350,229 B1 | 2/2002 | Borst et al. | |
| 6,352,531 B1 | 3/2002 | O'Conner et al. | |
| 6,352,552 B1 | 3/2002 | Levinson et al. | |
| 6,355,052 B1 | 3/2002 | Neuss et al. | |
| 6,364,826 B1 | 4/2002 | Borst et al. | |
| 6,371,906 B1 | 4/2002 | Borst et al. | |
| 6,375,671 B1 | 4/2002 | Kobayashi et al. | |
| 6,379,368 B1 | 4/2002 | Corcoran et al. | |
| 6,387,104 B1 | 5/2002 | Pugsley, Jr. et al. | |
| 6,394,948 B1 | 5/2002 | Borst et al. | |
| 6,398,796 B2 | 6/2002 | Levinson | |
| 6,401,720 B1 | 6/2002 | Stevens et al. | |
| 6,402,772 B1 | 6/2002 | Amplatz et al. | |
| 6,416,493 B1 | 7/2002 | Del Giglio | |
| 6,419,669 B1 | 7/2002 | Frazier et al. | |
| 6,432,059 B2 | 8/2002 | Hickey | |
| 6,436,088 B2 | 8/2002 | Frazier et al. | |
| 6,440,152 B1 | 8/2002 | Gainor et al. | |
| 6,458,100 B2 | 10/2002 | Roue et al. | |
| 6,464,640 B1 | 10/2002 | Guracar et al. | |
| 6,464,645 B1 | 10/2002 | Park et al. | |
| 6,482,224 B1 | 11/2002 | Michler et al. | |
| 6,482,228 B1 | 11/2002 | Norred | |
| 6,485,504 B1 | 11/2002 | Johnson et al. | |
| 6,488,706 B1 | 12/2002 | Solymar | |
| 6,497,698 B1 | 12/2002 | Fonger | |
| 6,532,388 B1 | 3/2003 | Hill et al. | |
| 6,537,300 B2 | 3/2003 | Girton | |
| 6,551,272 B2 | 4/2003 | Gobel | |
| 6,551,303 B1 | 4/2003 | Van Tassel et al. | |
| 6,551,344 B2 | 4/2003 | Thill | |
| 6,560,489 B2 | 5/2003 | Hauck | |
| 6,562,051 B1 | 5/2003 | Bolduc et al. | |
| 6,562,052 B2 | 5/2003 | Nobles et al. | |
| 6,572,593 B1 | 6/2003 | Daum | |
| 6,579,259 B2 | 6/2003 | Stevens et al. | |
| 6,585,716 B2 | 7/2003 | Altman | |

| | | |
|---|---|---|
| 6,592,552 B1 | 7/2003 | Schmidt |
| 6,592,557 B2 | 7/2003 | Barbut |
| 6,596,013 B2 | 7/2003 | Yang et al. |
| 6,606,513 B2 | 8/2003 | Lardo et al. |
| 6,613,062 B1 | 9/2003 | Leckrone et al. |
| 6,623,508 B2 | 9/2003 | Shaw et al. |
| 6,623,518 B2 | 9/2003 | Thompson et al. |
| 6,626,841 B1 | 9/2003 | Atlee, III |
| 6,626,890 B2 | 9/2003 | Nguyen et al. |
| 6,626,899 B2 | 9/2003 | Houser et al. |
| 6,626,930 B1 | 9/2003 | Allen et al. |
| 6,629,534 B1 | 10/2003 | St. Goar et al. |
| 6,632,223 B1 | 10/2003 | Keane |
| 6,645,225 B1 | 11/2003 | Atkinson |
| 6,650,923 B1 | 11/2003 | Lesh et al. |
| 6,651,672 B2 | 11/2003 | Roth |
| 6,656,206 B2 | 12/2003 | Corcoran et al. |
| 6,659,981 B2 | 12/2003 | Stewart et al. |
| 6,662,045 B2 | 12/2003 | Zheng et al. |
| 6,663,639 B1 | 12/2003 | Laufer et al. |
| 6,666,861 B1 | 12/2003 | Grabek |
| 6,679,268 B2 | 1/2004 | Stevens et al. |
| 6,685,728 B2 | 2/2004 | Sinnott et al. |
| 6,689,062 B1 | 2/2004 | Mesallum |
| 6,692,471 B2 | 2/2004 | Boudreaux |
| 6,692,512 B2 | 2/2004 | Jang |
| 6,695,838 B2 | 2/2004 | Wellman et al. |
| 6,699,231 B1 | 3/2004 | Sterman et al. |
| 6,702,835 B2 | 3/2004 | Ginn |
| 6,706,033 B1 | 3/2004 | Martinez et al. |
| 6,706,047 B2 | 3/2004 | Trout et al. |
| 6,712,804 B2 | 3/2004 | Roue et al. |
| 6,712,836 B1 * | 3/2004 | Berg et al. .............. 606/213 |
| 6,726,662 B2 | 4/2004 | Altman |
| 6,730,061 B1 | 5/2004 | Cuschieri et al. |
| 6,735,471 B2 | 5/2004 | Hill et al. |
| 6,736,828 B1 | 5/2004 | Adams et al. |
| 6,746,404 B2 | 6/2004 | Schwartz |
| 6,746,456 B2 | 6/2004 | Xiao |
| 6,749,617 B1 | 6/2004 | Palasís et al. |
| 6,773,441 B1 | 8/2004 | Laufer et al. |
| 6,776,784 B2 | 8/2004 | Ginn |
| 6,776,797 B1 | 8/2004 | Blom et al. |
| 6,783,499 B2 | 8/2004 | Schwartz |
| 6,790,218 B2 | 9/2004 | Jayaraman |
| 6,802,840 B2 | 10/2004 | Chin et al. |
| 6,821,265 B1 | 11/2004 | Bertolero et al. |
| 6,840,246 B2 | 1/2005 | Downing |
| 6,854,467 B2 | 2/2005 | Boekstegers |
| 6,855,116 B2 | 2/2005 | Atlee, III |
| 6,866,650 B2 | 3/2005 | Stevens et al. |
| 6,878,118 B2 | 4/2005 | Atlee, III |
| 6,882,883 B2 | 4/2005 | Condie et al. |
| 6,889,694 B2 | 5/2005 | Hooven |
| 6,899,704 B2 | 5/2005 | Sterman et al. |
| 6,902,545 B2 | 6/2005 | Bertolero et al. |
| 6,913,600 B2 | 7/2005 | Valley et al. |
| 6,913,607 B2 | 7/2005 | Ainsworth et al. |
| 6,915,149 B2 | 7/2005 | Ben-Haim |
| 6,918,890 B2 | 7/2005 | Schmidt |
| 6,918,908 B2 | 7/2005 | Bonner et al. |
| 6,929,011 B2 | 8/2005 | Knudson et al. |
| 6,932,792 B1 | 8/2005 | St. Goar et al. |
| 6,932,811 B2 | 8/2005 | Hooven et al. |
| 6,934,583 B2 | 8/2005 | Weinberg et al. |
| 6,939,348 B2 | 9/2005 | Malecki et al. |
| 6,939,361 B1 | 9/2005 | Kleshinski |
| 6,952,613 B2 | 10/2005 | Swoyer et al. |
| 6,953,466 B2 | 10/2005 | Palasis et al. |
| 6,955,175 B2 | 10/2005 | Steven et al. |
| 6,960,220 B2 | 11/2005 | Marino et al. |
| 6,971,998 B2 | 12/2005 | Rosenman et al. |
| 6,976,990 B2 | 12/2005 | Mowry |
| 6,991,635 B2 | 1/2006 | Takamoto et al. |
| 6,994,094 B2 | 2/2006 | Schwartz |
| 6,994,713 B2 | 2/2006 | Berg et al. |
| 7,001,415 B2 | 2/2006 | Hooven |
| 7,004,952 B2 | 2/2006 | Nobles et al. |
| 7,018,390 B2 | 3/2006 | Turovskiy et al. |
| 7,020,518 B2 | 3/2006 | Zheng et al. |
| 7,039,467 B2 | 5/2006 | Hauck |
| 7,044,135 B2 | 5/2006 | Lesh |
| 7,048,733 B2 | 5/2006 | Hartley et al. |
| 7,056,331 B2 | 6/2006 | Kaplan et al. |
| 7,083,628 B2 | 8/2006 | Bachman |
| 7,087,072 B2 | 8/2006 | Marino et al. |
| 7,090,683 B2 | 8/2006 | Brock et al. |
| 7,090,686 B2 | 8/2006 | Nobles et al. |
| 7,094,244 B2 | 8/2006 | Schreck |
| 7,097,653 B2 | 8/2006 | Freudenthal et al. |
| 7,101,395 B2 | 9/2006 | Tremulis et al. |
| 7,108,660 B2 | 9/2006 | Stephens et al. |
| 7,112,219 B2 | 9/2006 | Vidlund et al. |
| 7,113,831 B2 | 9/2006 | Hooven |
| 7,115,135 B2 | 10/2006 | Corcoran et al. |
| 7,186,251 B2 | 3/2007 | Malecki et al. |
| 7,507,252 B2 | 3/2009 | Lashinski et al. |
| 2001/0014800 A1 | 8/2001 | Frazier et al. |
| 2001/0034537 A1 | 10/2001 | Shaw et al. |
| 2001/0037129 A1 | 11/2001 | Thill |
| 2001/0039435 A1 | 11/2001 | Roue et al. |
| 2001/0041914 A1 | 11/2001 | Frazier et al. |
| 2001/0041915 A1 | 11/2001 | Roue et al. |
| 2001/0044639 A1 | 11/2001 | Levinson |
| 2001/0049492 A1 | 12/2001 | Frazier et al. |
| 2002/0010481 A1 | 1/2002 | Jayaraman |
| 2002/0019648 A1 | 2/2002 | Akerfeldt et al. |
| 2002/0026208 A1 | 2/2002 | Roe et al. |
| 2002/0032462 A1 | 3/2002 | Houser et al. |
| 2002/0035361 A1 * | 3/2002 | Houser et al. .............. 606/15 |
| 2002/0035374 A1 | 3/2002 | Borillo et al. |
| 2002/0039048 A1 | 4/2002 | Matsuge |
| 2002/0043307 A1 | 4/2002 | Ishida et al. |
| 2002/0052572 A1 | 5/2002 | Franco et al. |
| 2002/0077555 A1 | 6/2002 | Schwartz |
| 2002/0096183 A1 | 7/2002 | Stevens et al. |
| 2002/0099389 A1 | 7/2002 | Michler et al. |
| 2002/0099437 A1 | 7/2002 | Anson et al. |
| 2002/0107531 A1 | 8/2002 | Schreck et al. |
| 2002/0111637 A1 | 8/2002 | Kaplan et al. |
| 2002/0111647 A1 | 8/2002 | Khairkhahan et al. |
| 2002/0120323 A1 | 8/2002 | Thompson et al. |
| 2002/0128680 A1 | 9/2002 | Pavlovic |
| 2002/0129819 A1 | 9/2002 | Feldman et al. |
| 2002/0138095 A1 | 9/2002 | Mazzocchi et al. |
| 2002/0169377 A1 | 11/2002 | Khairkhahan et al. |
| 2002/0183786 A1 | 12/2002 | Girton |
| 2002/0183787 A1 * | 12/2002 | Wahr et al. .............. 606/213 |
| 2002/0183823 A1 | 12/2002 | Pappu |
| 2002/0198563 A1 | 12/2002 | Gainor et al. |
| 2003/0025421 A1 | 2/2003 | Ebihara et al. |
| 2003/0028213 A1 * | 2/2003 | Thill et al. .............. 606/200 |
| 2003/0033006 A1 | 2/2003 | Phillips et al. |
| 2003/0045893 A1 | 3/2003 | Ginn |
| 2003/0050665 A1 | 3/2003 | Ginn |
| 2003/0059640 A1 | 3/2003 | Marton et al. |
| 2003/0100920 A1 | 5/2003 | Akin et al. |
| 2003/0139819 A1 | 7/2003 | Beer et al. |
| 2003/0144694 A1 | 7/2003 | Chanduszko et al. |
| 2003/0167071 A1 | 9/2003 | Martin et al. |
| 2003/0191495 A1 | 10/2003 | Ryan et al. |
| 2003/0195530 A1 | 10/2003 | Thill |
| 2003/0195555 A1 | 10/2003 | Khairkhahan et al. |
| 2003/0204203 A1 | 10/2003 | Khairkhahan et al. |
| 2003/0208232 A1 | 11/2003 | Blaeser et al. |
| 2003/0225421 A1 | 12/2003 | Peavey et al. |

| | | | |
|---|---|---|---|
| 2004/0044361 A1 | 3/2004 | Frazier et al. |
| 2004/0073242 A1 | 4/2004 | Chanduszko |
| 2004/0092973 A1 | 5/2004 | Chanduszko et al. |
| 2004/0098042 A1 | 5/2004 | Devellian et al. |
| 2004/0098121 A1 | 5/2004 | Opolski |
| 2004/0133230 A1 | 7/2004 | Carpenter et al. |
| 2004/0133236 A1 | 7/2004 | Chanduszko |
| 2004/0176799 A1 | 9/2004 | Chanduszko et al. |
| 2004/0210301 A1 | 10/2004 | Obermiller |
| 2004/0220596 A1 | 11/2004 | Frazier et al. |
| 2004/0243122 A1 | 12/2004 | Auth et al. |
| 2004/0267191 A1 | 12/2004 | Gifford, III et al. |
| 2004/0267306 A1 | 12/2004 | Blaeser et al. |
| 2005/0034735 A1 | 2/2005 | Deem et al. |
| 2005/0043759 A1 | 2/2005 | Chanduszko |
| 2005/0055050 A1 | 3/2005 | Alfaro |
| 2005/0059984 A1 | 3/2005 | Chanduszko et al. |
| 2005/0070923 A1 | 3/2005 | McIntosh |
| 2005/0080406 A1 | 4/2005 | Malecki et al. |
| 2005/0119675 A1 | 6/2005 | Adams et al. |
| 2005/0125032 A1 | 6/2005 | Whisenant et al. |
| 2005/0131460 A1 | 6/2005 | Gifford, III et al. |
| 2005/0149115 A1 | 7/2005 | Roue et al. |
| 2005/0187568 A1 | 8/2005 | Klenk et al. |
| 2005/0187588 A1 | 8/2005 | Stahmann et al. |
| 2005/0187620 A1 | 8/2005 | Pai et al. |
| 2005/0192626 A1 | 9/2005 | Widomski et al. |
| 2005/0192627 A1 | 9/2005 | Whisenant et al. |
| 2005/0192654 A1 | 9/2005 | Chanduszko et al. |
| 2005/0209636 A1 | 9/2005 | Widomski et al. |
| 2005/0216054 A1 | 9/2005 | Widomski et al. |
| 2005/0228434 A1 | 10/2005 | Amplatz et al. |
| 2005/0234509 A1 | 10/2005 | Widomski et al. |
| 2005/0251154 A1 | 11/2005 | Chanduszko et al. |
| 2005/0251201 A1 | 11/2005 | Roue et al. |
| 2005/0256532 A1 | 11/2005 | Nayak et al. |
| 2005/0267495 A1 | 12/2005 | Ginn et al. |
| 2005/0267523 A1 | 12/2005 | Devellian et al. |
| 2005/0267524 A1 | 12/2005 | Chanduszko |
| 2005/0267525 A1 | 12/2005 | Chanduszko |
| 2005/0267526 A1 | 12/2005 | Wahr et al. |
| 2005/0271631 A1 | 12/2005 | Lee et al. |
| 2005/0273119 A1 | 12/2005 | Widomski et al. |
| 2005/0273124 A1 | 12/2005 | Chanduszko |
| 2005/0273135 A1 | 12/2005 | Chanduszko et al. |
| 2005/0277982 A1 | 12/2005 | Marino et al. |
| 2005/0288706 A1 | 12/2005 | Widomski et al. |
| 2005/0288786 A1 | 12/2005 | Chanduszko |
| 2006/0009800 A1 | 1/2006 | Christianson et al. |
| 2006/0015002 A1 | 1/2006 | Moaddeb et al. |
| 2006/0036282 A1 | 2/2006 | Wahr et al. |
| 2006/0036284 A1 | 2/2006 | Blaeser et al. |
| 2006/0052821 A1 | 3/2006 | Abbott et al. |
| 2006/0069408 A1 | 3/2006 | Kato |
| 2006/0079870 A1 | 4/2006 | Barry |
| 2006/0200197 A1 | 9/2006 | Brenzel et al. |
| 2006/0271089 A1 | 11/2006 | Alejandro et al. |
| 2007/0005018 A1 | 1/2007 | Tekbuchava |
| 2007/0010806 A1 | 1/2007 | Malecki et al. |
| 2007/0049970 A1 | 3/2007 | Belef et al. |
| 2007/0073337 A1 | 3/2007 | Abbott et al. |
| 2007/0123851 A1 | 5/2007 | Alejandro et al. |
| 2007/0185530 A1 | 8/2007 | Chin-Chen et al. |

FOREIGN PATENT DOCUMENTS

| | | |
|---|---|---|
| EP | 0 553 259 B1 | 3/1995 |
| EP | 1 013 227 A2 | 6/2000 |
| EP | 1 222 897 A2 | 7/2002 |
| EP | 1 046 375 B1 | 11/2004 |
| JP | 04-226643 | 8/1992 |
| WO | WO 92/05828 A1 | 4/1992 |
| WO | WO 92/06733 A1 | 4/1992 |
| WO | WO 96/25179 A1 | 8/1996 |
| WO | WO 96/31157 A1 | 10/1996 |
| WO | WO 97/42878 A1 | 11/1997 |
| WO | WO 98/02100 A1 | 1/1998 |
| WO | WO 98/07375 A1 | 2/1998 |
| WO | WO 99/02100 A1 | 1/1999 |
| WO | WO 99/18862 A1 | 4/1999 |
| WO | WO 99/18864 A1 | 4/1999 |
| WO | WO 99/18870 A1 | 4/1999 |
| WO | WO 99/18871 A1 | 4/1999 |
| WO | WO 00/07506 A2 | 2/2000 |
| WO | WO 00/27292 A1 | 5/2000 |
| WO | WO 00/35352 A2 | 6/2000 |
| WO | WO 00/44428 A2 | 8/2000 |
| WO | WO 01/21247 A1 | 3/2001 |
| WO | WO 01/49185 A1 | 7/2001 |
| WO | WO 01/78596 A1 | 10/2001 |
| WO | WO 02/24106 A2 | 3/2002 |
| WO | WO 02/062236 A1 | 8/2002 |
| WO | WO 03/059152 A2 | 7/2003 |
| WO | WO 03/063732 A2 | 8/2003 |
| WO | WO 03/077733 A2 | 9/2003 |
| WO | WO 03/094742 A1 | 11/2003 |
| WO | WO 03/103476 A2 | 12/2003 |
| WO | WO 2004/026146 A1 | 4/2004 |
| WO | WO 2004/043266 A2 | 5/2004 |
| WO | WO 2004/052213 A1 | 6/2004 |
| WO | WO 2004/069055 A2 | 8/2004 |
| WO | WO 2004/086951 A2 | 10/2004 |
| WO | WO 2004/087235 A2 | 10/2004 |
| WO | WO 2005/006990 A2 | 1/2005 |
| WO | WO 2005/027752 A1 | 3/2005 |
| WO | WO 2005/034738 A2 | 4/2005 |
| WO | WO 2005/039419 A1 | 5/2005 |
| WO | WO2005/039419 A1 | 5/2005 |
| WO | WO 2005/074517 A2 | 8/2005 |
| WO | WO 2005/074814 A2 | 8/2005 |
| WO | WO 2005/082255 A1 | 9/2005 |
| WO | WO 2005/092203 A1 | 10/2005 |
| WO | WO 2005/110240 A1 | 11/2005 |
| WO | WO 2005/112779 A1 | 12/2005 |
| WO | WO 2006/036837 A2 | 4/2006 |
| WO | WO 2007/024615 A1 | 3/2007 |
| WO | WO 2008/024489 A2 | 2/2008 |
| WO | WO 2008/153872 A2 | 12/2008 |

OTHER PUBLICATIONS

U.S. Appl. No. 10/734,670; Non-Final Office Action, Mailed Jan. 12, 2009.

Baim, D., Percutaneous Approach, Including Transseptal and Apical Puncture, Grossman's Cardiac Catheterization, Angiography, and Intervention, 6th Ed., 2000.

Daoud, E., et al. Intracardiac Echocardiography to Guide Transseptal Left Heart Catheterization for Radiofrequency Catheter Ablation, Journal of Cardiovascular Electrophysiology, vol. 10, No. 3, Mar. 1999.

De Ponti, R., et al., Trans-septal catheterization for radiofrequency catheter ablation of cardiac arrhythmias, European Heart Journal, vol. 19, 1998.

Epstein, L., et al., Nonfluoroscopic Transseptal Catheterization: Safety and Efficacy of Intracardiac Echocardiographic Guidance, Journal of Cardiovascular Electrophysciology, vol. 9, No. 6, Jun. 1998.

Hara, H., et al., Patent Foramen Ovale: Current Pathology, Pathophysiology, and Clinical Status, Journal of the American College of Cardiology, vol. 46, No. 9, Nov. 2005:1768-1776.

Hurrell, D., et al., Echocardiography in the Invasive Laboratory: Utility of Two-Dimensional Echocardiography in Performing Transseptal Catherization, Mayo Clinic Proc., 1998:73:126-131.

Lesh, M., et al., Comparison of the Retrograde and Transseptal Methods for Ablation of Left Free Wall Accessory Pathways, Journal of American College of Cardiology, vol. 22, No. 2, Aug. 1993:542-549.

Lundqvist, C., et al., Transseptal Left Heart Catheterization: A Review of 278 Studies, Clin. Cardiol. 9, Jan. 1986.

Mitchel, J., et al., Intracardiac Ultrasound Imaging During Transseptal Catheterization, Chest, vol. 108, No. 1, Jul. 1995.

Montenero, A., et al., Catheter Ablation of Left Accessory Atrioventricular Connections: The Transseptal Approach, Journal of Interventional Cardiology, vol. 8, No. 6 (Suppl), 1995.

Peckham, G., et al., Combined Percutaneous Retrograde Aortic and Transseptal Left Heart Catheterization, Brit. Heart Journal, vol. 26, 1964.

Reig, J., et al., Morphologic characteristics of the fossa ovalis as an anatomic basis for transseptal catheterization, Surg. Radiol. Anat. vol. 19, No. 5, 1997.

Roelke, M., et al., The Technique and Safety of Transseptal Left Heart Catheterization: The Massachusetts General Hospital Experience With 1,279 Procedures, Catheterization and Cardiovascular Diagnosis, vol. 32, No. 4, Aug. 1994.

Szili-Torok, T., Transseptal left heart catherisation guided by intracardiac echocardiography, Heart, vol. 86, e. 11, 2001.

Tucker, K., Transesophageal Echocardiographic Guidance of Transseptal Left Heart Catheterization During Radiofrequency Ablation of Left-Sided Accessory Pathways in Humans, PACE, vol. 19, Mar. 1996.

St. Jude Medical, BRK™ Transseptal Needle (Instructions for Use), Nov. 2006.

* cited by examiner

CLIP APPARATUS FOR CLOSING SEPTAL DEFECTS AND METHODS OF USE

CROSS-REFERENCE TO RELATED APPLICATIONS

This application is a continuation of and claims priority to U.S. application Ser. No. 09/948,502 filed Sep. 6, 2001 now U.S. Pat. No. 6,776,784, the disclosure of which is fully incorporated herein by reference.

FIELD OF THE INVENTION

The present invention relates generally to apparatus and methods for treating septal defects, and more particularly to apparatus and methods for closing a patent foramen ovale or other septal defect.

BACKGROUND

During development of a fetus in utero, blood is generally oxygenated by the mother's placenta, not the fetus' developing lungs. Most of the fetus' circulation is shunted away from the lungs through specialized vessels or foramens that are open during fetal life, but generally close shortly after birth. Occasionally, however, these foramen fail to close and create hemodynamic problems, which may ultimately prove fatal unless treated.

One defect that may occur is a patent foramen ovale ("PFO"), which may occur between the left and right atria of the heart. During fetal life, an opening called the foramen ovale allows blood to pass directly from the right atrium to the left atrium (bypassing the lungs). Thus, oxygenated blood from the placenta may travel through the vena cava into the right atrium, through the foramen ovale into the left atrium, and from there into the left ventricle for delivery via the aorta to the fetus' body. After birth, with pulmonary circulation established, the increased left atrial blood flow and pressure causes the functional closure of the foramen ovale. This closure is then followed by the anatomical closure of the foramen ovale.

In some humans, however, the foramen ovale fails to completely close. This condition can pose serious health risks for the individual, particularly if the individual has other heart abnormalities. For example, recent studies suggest an association between the presence of a patent foramen ovale and the risk of paradoxical embolism or stroke. See P. Lechat J et al., *Prevalence of Patent Foramen ovale in Patients with Stroke*, N. Engl. J. Med. 1988;318: 1148-1152.

Still other septal defects may occur within a septum between the various chambers of the heart, such as atrial-septal defects (ASDs), ventricular-septal defects (VSDs), and the like. To close such defects, open heart surgery may be performed to ligate and close the defect. Such procedures are obviously highly invasive and pose substantial morbidity and mortality risks.

Alternatively, catheter-based procedures have been suggested. These may involve introducing umbrella or disk-like structures into the heart that include opposing expandable structures connected by a hub or waist. Generally, the device is inserted through the defect, and the expandable structures are deployed on either side of the septum to secure the tissue surrounding the defect between the umbrella or disk-like structure in an attempt to seal and close the defect. Such devices, however, involve frame structures that often support membranes, either of which may fail during the life of the patient being treated, opening the defect and/or releasing segments of the structure within the patient's heart.

Accordingly, apparatus and methods for closing septal defects, and in particular a patent foramen ovale, would be considered useful.

SUMMARY OF THE INVENTION

The present invention is directed to apparatus and methods for closing septal defects, including, but not limited to, a patent foramen ovale.

In a first aspect of the invention, an apparatus for closing a septal defect includes a clip formed from a elastic material having at least two penetrating tines and an opposing retaining end. The clip is biased so as to project the at least two penetrating tines distal to the opposing retaining end, wherein when the bias is removed, the at least two penetrating tines move laterally apart from one another.

In accordance with another aspect of the present invention, a delivery apparatus for delivering a clip, such as that described above, is provided that includes an outer catheter and a pusher member that are slidably coupled to one another. The catheter may be a tubular member including proximal and distal ends and a lumen therebetween, the distal end having a size for insertion into a blood vessel or other body lumen. The clip may be carried within the lumen of the outer catheter, preferably, with the tines disposed distally to the retaining end.

The pusher member may be an inner catheter or other elongate member that is disposed within the lumen of the outer catheter. The pusher member may include a distal end that may be disposed proximate the retaining end of the clip, the pusher member being movable axially relative to the tubular member for ejecting the clip distally from the lumen.

An actuator may be provided on the proximal end of the tubular member and/or the pusher member for advancing the pusher member relative to the tubular member. Preferably, the actuator may limit advancement of the pusher member.

In a further alternative, the delivery apparatus may include an imaging device including an imaging element associated with the distal end of the tubular member for imaging near or beyond the distal end of the tubular member. For example, the imaging device may be an angioscope or ultrasound device that may be received within a lumen of the tubular member or may be a separate device that may introduced independently into the patient but used in conjunction with the delivery apparatus during a procedure.

In another alternative, the clip has a single tine and an opposing retaining end. The clip is biased so as to project the single tine distal to the opposing retaining end. When the bias is removed, the clip transforms into a geometric shape such as a "V", "U", "S", or "L". The opposing retaining end may have an optional head to prevent the clip from completely passing through the septum wall of a heart.

In accordance with yet another aspect of the present invention, a method is provided for closing a patent foramen ovale or other septal defect within a patient's heart. Generally, the septal defect includes one or more flaps of tissue partially detached from a septum wall between first and second chambers of the heart, the flap(s) of tissue and surrounding tissue of the septum wall defining a septal opening through the septum wall.

A clip, such as that described above, is advanced, in a stressed state, through the patient's vasculature until the clip is disposed adjacent to the septal opening. The tines of the clip penetrate the flap of tissue and pass into the second chamber of the heart. After the clip has penetrated the flap of tissue (i.e., septal defect), the clip transitions to its relaxed state so as to at least partially close the septal opening.

It is an object of the invention to provide a clip apparatus for the closure of septal defects, such as a patent foramen ovale. It is a further object of the invention to provide a delivery device for the delivery of the clip apparatus to the defect area. It is yet a further object of the invention to provide a method of closing a patent foramen ovale using the clip apparatus. Other objects and features of the present invention will become apparent from consideration of the following description taken in conjunction with the accompanying drawings.

DETAILED DESCRIPTION OF THE PREFERRED EMBODIMENTS

Figure 1:
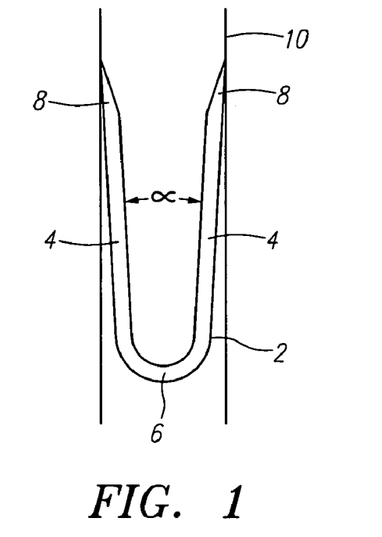
FIG. 1 is a cross-sectional view of a clip apparatus showing the clip in a stressed state.
Figure 2:
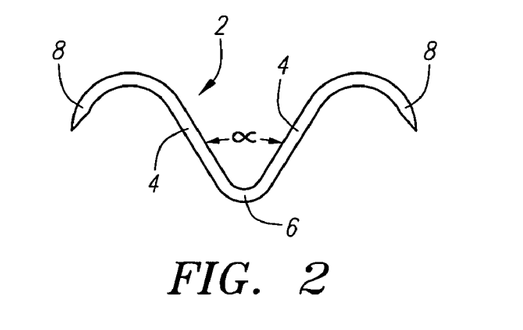
FIG. 2 is a cross-sectional view of the clip shown in FIG. 1 with the clip in a relaxed state.

FIGS. 1 and 2 illustrate a first preferred embodiment of a clip 2 that is used for closing a septal defect (i.e., PFO, ASA, VSA), in accordance with the present invention. The clip 2 includes two penetrating tines 4 that are connected to one another via an opposing retaining end 6. The tips 8 of the tines 4 are sharpened to aid in penetrating tissue. In FIG. 1, the clip 2 is shown in its stressed state. In this regard, the clip 2 may by made from an elastic material, such as stainless steel, and preferably, a superelastic material. Alternatively, the clip 2 may be formed from a shape memory alloy, one example being NITINOL. Of course, other bio-compatible elastic or superelastic materials may also be employed. The clip 2 is maintained in its stressed state by restraining the tines 4 from expanding outward. In this manner a biasing force is applied to the clip 2. The tines 4 of the clip 2 project distally from the retaining end 6, as is shown, for example, in FIG. 1. The tines 4 preferably are restrained by using a delivery apparatus 10, such as a catheter or the like (discussed in more detail below). Preferably, in its stressed state, the clip 2 has the shape of a "U" or a "V", as is shown, for example, in FIG. 1.

FIG. 2 illustrates the clip 2 in its relaxed state. Without the application of the biasing force, the clip 2 transitions to its related configuration wherein the angle α between the two tines 4 increases. The tines 4 also move laterally away from one another, as is shown, for example, in FIG. 2. In addition, portions of the tines 4 closest to the tips 8 may optionally inflect back upon themselves. In one preferred embodiment, in the final relaxed configuration, the clip 2 preferably has the shape of a "W", as is shown, for example, in FIG. 2.

Depending on the type and nature of the septal defect, the clip 2 may have variations in its design. For example, the length of the tines 4 may be chosen depending on the size of the opening 42. If the opening is larger, longer tines 4 may be used. Similarly, a larger opening 42 may require a greater expansion angle α for the clip. Other variations may also be present, such as the degree of inflection, if any, in the ends of the tines 4 nearest the tips 8. The clip 2 may be made of one piece of material or, alternatively, multiple segments.

Figure 3:
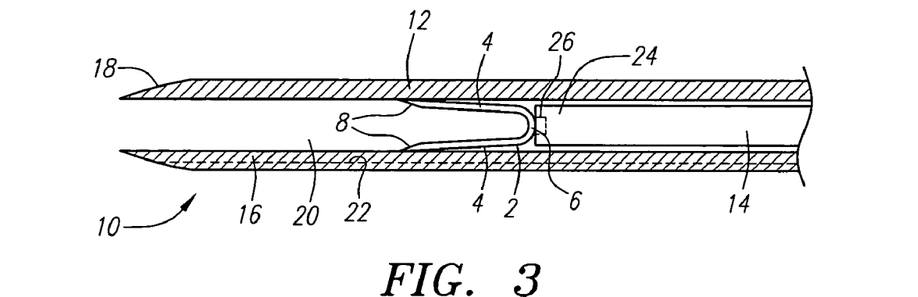
FIG. 3 is a cross-sectional view of a delivery apparatus showing a pusher member and a clip contained within a lumen of the delivery apparatus.

Referring now to FIG. 3, a delivery apparatus 10 generally includes an outer catheter or tubular member 12, and an inner catheter or pusher member 14. The outer catheter 12 includes a proximal end (not shown), and a distal end 16 having a size suitable for insertion into a blood vessel or other body lumen (not shown). The distal end 16 preferably has a tapered or rounded tip 18, e.g., for facilitating substantial atraumatic advancement of the delivery apparatus 10 through the patient's vasculature. The outer catheter 12 also includes a lumen 20 therein that extends between proximal and distal ends 16. As shown in FIG. 3, the clip 2 is contained within the lumen 20 of the outer catheter 12. The outer catheter 12 provides the biasing force to keep the clip 2 in its stressed state.

In one preferred embodiment of the invention, the outer tubular member 12 may include one or more axially disposed grooves 22 (one is shown in FIG. 3) within the inner surface that engages with the tine(s) 4 of the clip 2. The groove(s) 22 may serve as a guide for the clip 2 so that the orientation of the clip 2 is maintained during delivery. In this regard, the clip 2 may not rotate into a different orientation as it is ejected from the outer catheter 12.

The pusher member 14 includes a proximal end (not shown) and a distal end 24 having a size such that the pusher member 14 may be slidably disposed within the lumen 20 of the outer catheter 12. The distal end 24 may be disposed proximal to the retaining end 6 of the clip 2, and the pusher member 14 may be moveable axially relative to the outer catheter 12 for ejecting the clip 2 distally from the lumen 20, as is described more fully below. Optionally, the distal end 24 of the pusher member 14 may contain a notch 26 that engages with the retaining end 6 of the clip 2 for assisting in orienting of the clip 2. The notch 26 may prevent the rotation of the clip 2, or alternatively, aid in rotating the clip 2 (through rotation of the pusher member 14) for proper orientation. The notch 26 may be present without or in addition to the groove(s) 22.

An actuator, e.g., a handle device (not shown), may be provided on the proximal end of the outer catheter 12 and/or the pusher member 14.

Figure 4:
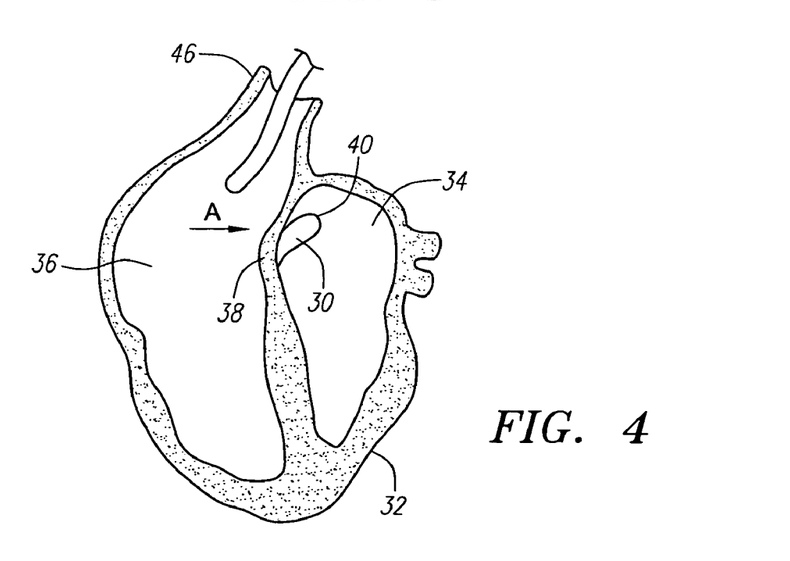
FIG. 4 is a cross-sectional view of a heart including a septal foramen ovale in a septum wall of the heart. The delivery apparatus of FIG. 3 is shown being advanced through the aortic arch.
Figure 5:
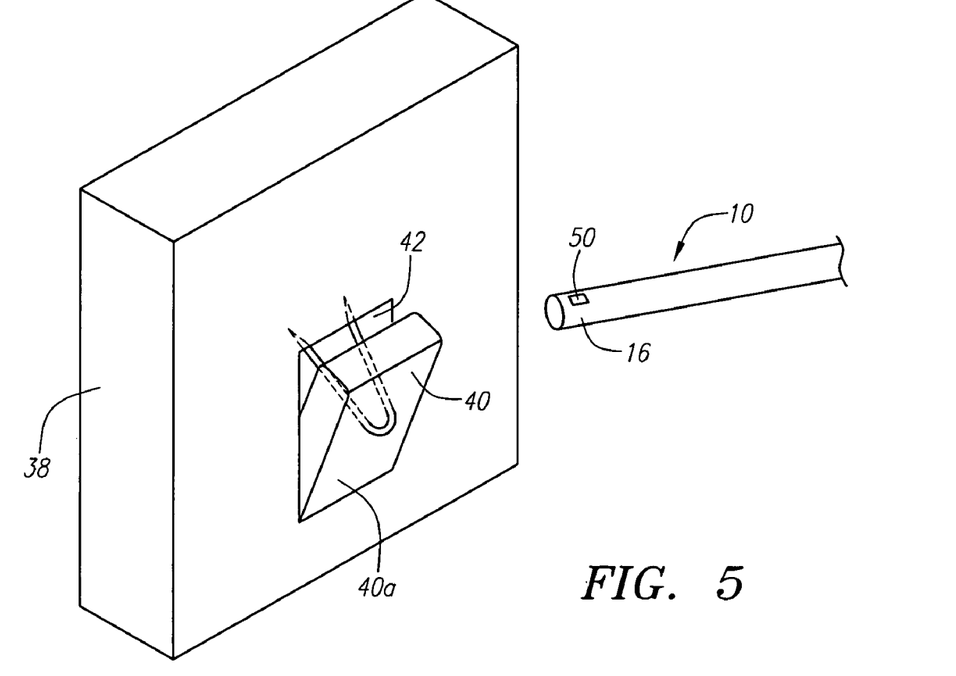
FIG. 5 is a perspective detail view of the septal defect shown in FIG. 4. A flap of tissue, which is partially attached to the septum, has been pierced by the clip in its stressed state.
Figure 6:
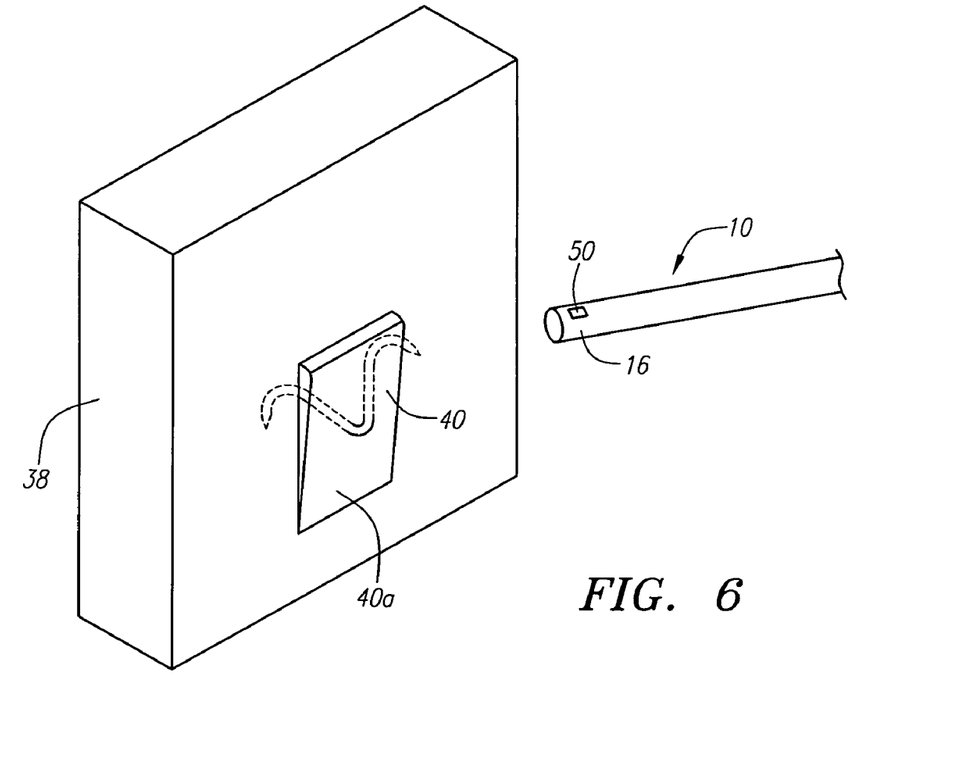
FIG. 6 is a perspective detail view of the septal defect shown in FIG. 4 after deployment of the clip apparatus. The flap of tissue has closed the opening after the clip has transitioned to its relaxed state.
Figure 10:
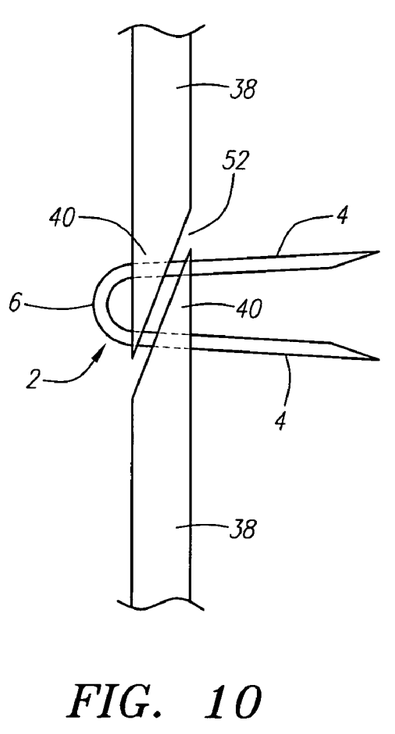
FIG. 10 is a cross-sectional view of the septum wall showing a hole-type septal defect. The clip is shown in its stressed state.
Figure 11:
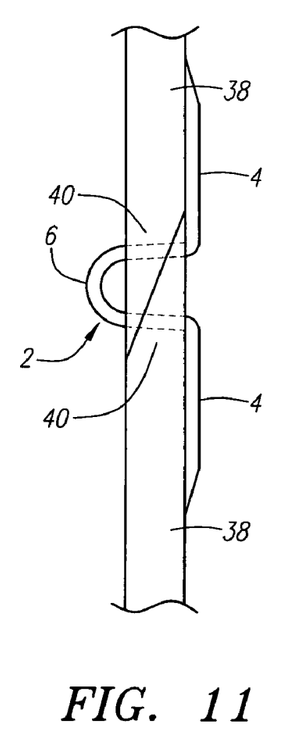
FIG. 11 is a cross-sectional view of the septum wall showing a hole-type septal defect. The clip is shown in its relaxed state.

Use of the clip 2 for closing a septal defect 30 is shown in conjunction with FIGS. 4-7(c), 10, and 11. FIG. 4 generally shows a heart 32 of a patient, including heart chambers 34, 36 separated by a septum wall 38. The septal defect 30, which may be a PFO, ASD, VSD and the like, is shown in the septum wall 38. As best seen in FIGS. 5 and 6, the septal defect 30 may include a flap of tissue 40 adjacent to an opening 42 in the septum wall 38. FIGS. 10 and 11 illustrate another septal defect 30 wherein the defect is a hole-type of structure 52, e.g., extending laterally through the septum wall 38.

The delivery apparatus 10, with the clip 2 therein, may be introduced into the patient's vasculature, e.g., from a percutaneous entry site in a peripheral vessel, such as the femoral vein, jugular vein, and the like (not shown). The distal end of the outer catheter 12, including the clip 2, may be advanced endoluminally within the patient's vasculature, e.g., through the vena cava 46 (inferior or superior) and into the heart 32 until the distal end 16 is disposed within the chamber 34, which is shown in FIG. 4 to be the right atrium. Alternatively, the clip 2 may be introduced using an arterial approach as is commonly known in the art.

Figure 7A:
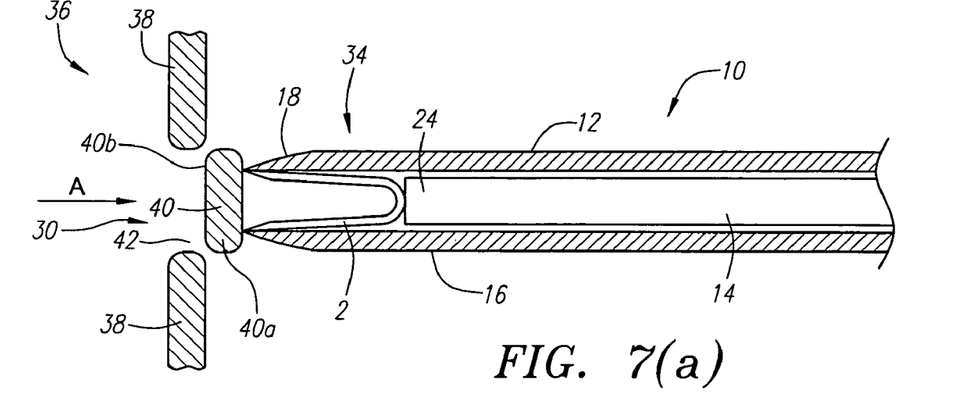
FIG. 7(a) is a cross-sectional view of the septum wall and delivery device, showing a method for closing the septal defect shown in FIGS. 4-6. The delivery device is shown adjacent to the flap of tissue.

With particular reference to FIGS. 5, 6, and 7(a)-(c), the distal end 16 of the delivery apparatus 10 may be advanced into contact with a proximal surface 40a of the flap of tissue 40, e.g., such that the flap of tissue 40 is disposed proximate the septal opening 42, as shown in FIG. 7(a). The pusher member 14 may be advanced distally relative to the outer catheter 12, thereby piercing the tines 4 of the clip 2 through the flap of tissue 40 until a portion of the tines 4 of the clip 2 are located within the second chamber 36 located on the opposing side of the septum wall 38, thereby creating punctures 48 for each tine 4. The penetrating tips 8 on the tines 4 of the clip are preferably sharp enough to facilitate piercing and passing of the tines 4 through the flap of tissue 40.

Figure 7B:
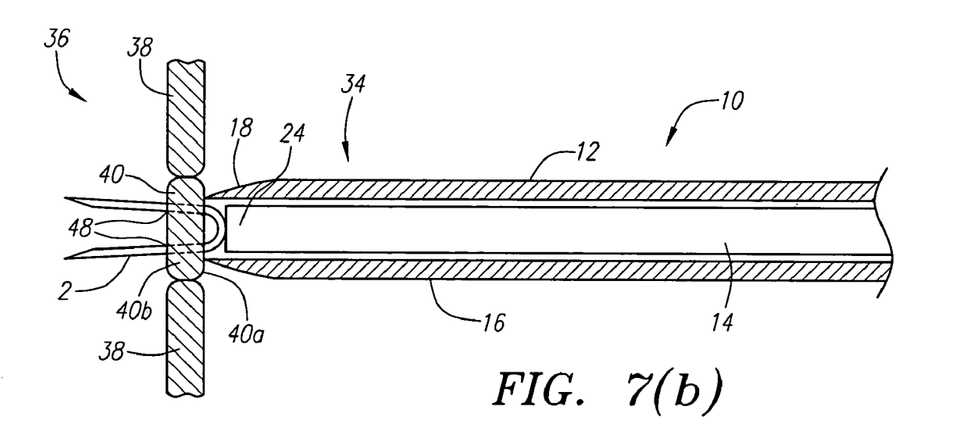
FIG. 7(b) is a cross-sectional view of the septum wall and delivery device, showing a method for closing the septal defect shown in FIGS. 4-6. The pusher member has deployed the clip through the flap of tissue.
Figure 7C:
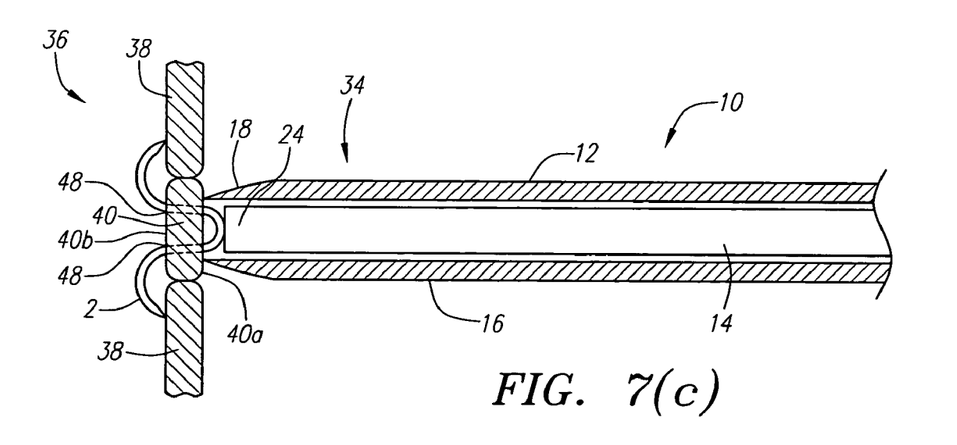
FIG. 7(c) is a cross-sectional view of the septum wall and delivery device, showing a method for closing the septal defect shown in FIGS. 4-6. The clip has transitioned to its relaxed state and closed the septal defect.

Preferably, the pusher member 14 is advanced distally to aid in pushing the tines 4 of the clip 2 through the flap of tissue 40. The pusher member 14 preferably pushes until the clip 2 cannot advance further through the flap of tissue 40 (i.e., the retaining end 6 of the clip 2 prevents further advancement). This may be accomplished by using an actuator (not shown) on the delivery apparatus 10 that permits controlled advancement of the pusher member 14. For example, the actuator may allow the distal end 24 of the pusher member 14 to be disposed at a location within or external to the distal tip 18 of the outer catheter 12.

FIG. 7(b) shows the clip 2, still in its stressed state, puncturing the flap of tissue 40. The nature of the material of the clip 2 is such that the clip 2 remains in the stressed state as the tines 4 pierce the flap of tissue 40. After the clip 2 has passed through the flap of tissue 40, the clip 2 begins its transformation from the stressed state to the relaxed state shown, for example, in FIG. 2. FIG. 7(c) shows the clip 2 after it has passed into the relaxed state. In this embodiment, the tips 8 of the tines 4 have inflected back in the direction of the retaining end 6 of the clip 2. In doing so, the tips 8 of the clip 2 preferably engage with the septum wall 38 on opposing sides of the flap of tissue 40. While it is preferable that both tips 8 be engaged with the septum wall 38 to properly close the opening 42, it may still be possible to close the opening 42 if only one of the tips 8 engages with the septum wall 38.

As best seen in FIG. 6, in which a perspective detail view of the region of the septum wall 38 having the septal defect 30 is shown, the opening 42 between the first and second chambers 34, 36 has been eliminated by the placement of the clip 2 in the flap of tissue 40. By engaging with the septum wall 38, the tips 8 of the clip 2 may prevent the flap of tissue 40 from moving proximate to the septum wall 38 in the first chamber 34 (as is shown in FIG. 7(a)).

Figure 8:
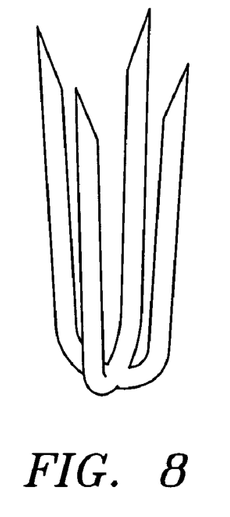
FIG. 8 is a perspective view of a clip according to a separate preferred aspect of the invention. The clip is shown in its stressed state.
Figure 9:
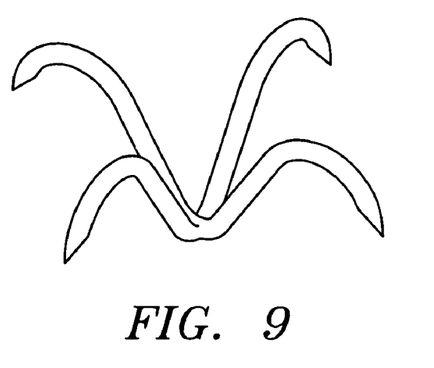
FIG. 9 is a perspective view of the clip shown in FIG. 8 with the clip in its relaxed state.

FIGS. 8 and 9 show an alternative preferred embodiment of the clip 2 wherein the clip 2 has four tines 4 as opposed to the two tines 4 shown in FIGS. 1-7(c), 10, and 11. FIG. 8 shows the clip 2 in a stressed state while FIG. 9 shows the clip 2 in a relaxed state. The additional tines 4 may increase the chances that one or more tines 4 will properly be secured to the septum wall 38 upon deployment. While clips 2 having two and four tines 4 have been specifically disclosed herein, it should be understood that the clip 2 may have any number of tines 4 in excess of one, including even and odd numbers of tines 4.

It will be appreciated by those skilled in the art that the procedure described herein may be monitored in a variety of ways. For example, the delivery apparatus 10 may include an imaging device 50 (FIGS. 5 and 6), such as an angioscope or other fiber optic device, intravascular ultrasound ("IVUS") device, and the like (not shown). The device may be provided on the distal end 16 of the outer catheter 12, e.g., attached to or adjacent the distal tip 18 or advanceable from a lumen (not shown) therein. In a further alternative, external imaging may be used, either alone or in conjunction with direct visualization. For example, the clip 2, the outer catheter 12, and/or the pusher member 14 may include radiopaque markers (not shown) at predetermined locations that may be observed using fluoroscopy and the like.

FIGS. 10 and 11 illustrate a preferred embodiment of the clip 2, wherein in its relaxed state (shown in FIG. 11), the tines 4 of the clip 2 lie substantially flat against the septum wall 38. This embodiment may be preferred for several reasons. First, a larger portion of the tines 4 may be in contact with the septum wall 38, giving the clip 2 a more secure hold to the flap(s) of tissue 40. Second, since at least a portion of the tines 4 lie substantially flat against the septum wall 38, less surface area of the clip 2 may be exposed to the patient's blood. Typically, a patient that receives a clip 2 may be administered anti-coagulant drugs to counteract the clotting of platelets on the surface of the clip 2. By reducing the amount of surface area of the clip 2 that is exposed to the blood, clotting problems may be reduced. FIG. 11 shows a cross-sectional view of the septum wall 38 with the clip 2 in its relaxed state. Preferably, the clip 2 is designed such that the tines 4 of the clip 2 lie substantially flat against the septum wall 38 on either side of the septal defect 30.

FIGS. 10 and 11 further illustrate the septum wall 38 containing a septal defect 30 in which the defect is a hole-type structure 52 that may pass laterally through the septum wall 38 of a heart 32. In this regard, the septal defect 30 is similar to two overlapping flaps of tissue 40. This type of septal defect 30 may be seen, for example, in patients having a PFO. The clip 2 may be delivered in a similar way to the method described above. Specifically, the clip 2 may puncture the two overlapping flaps of tissue 40 while the clip 2 is in its stressed state and, upon relaxation, at least a portion of the hole-type structure 52 may collapse, thereby preventing the flow of blood across the septum wall 38.

Figure 12A:
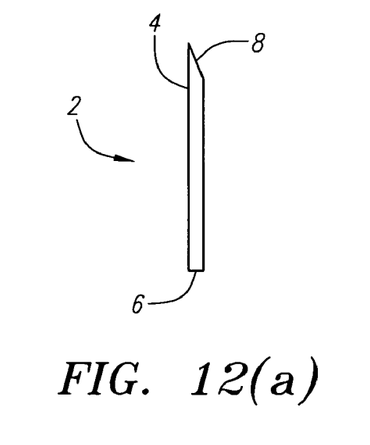
FIG. 12 is a cross-sectional view of the septum wall showing a hole-type septal defect. A clip having a single tine is shown in its relaxed state.
Figure 12B:
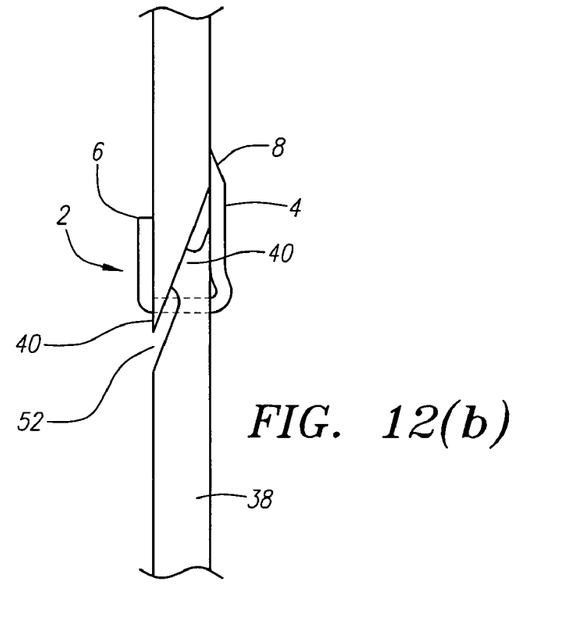
Figure 13:
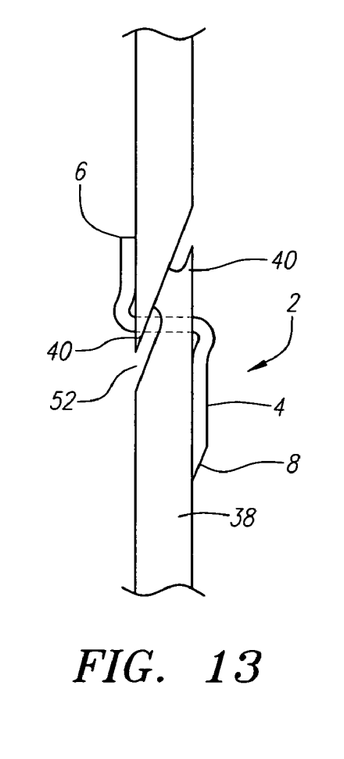
FIG. 13 is a cross-sectional view of the septum wall showing a hole-type septal defect. A clip having a single tine is shown in its relaxed state.
Figure 14A:
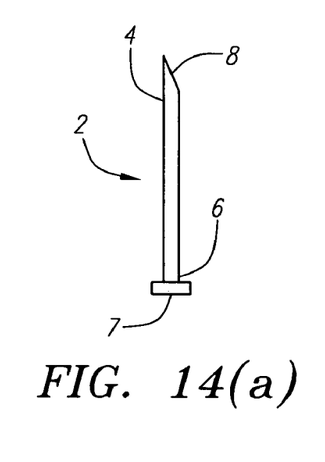
FIG. 14 is a cross-sectional view of the septum wall showing a hole-type septal defect. A clip having a single tine is shown in its relaxed state.
Figure 14B:
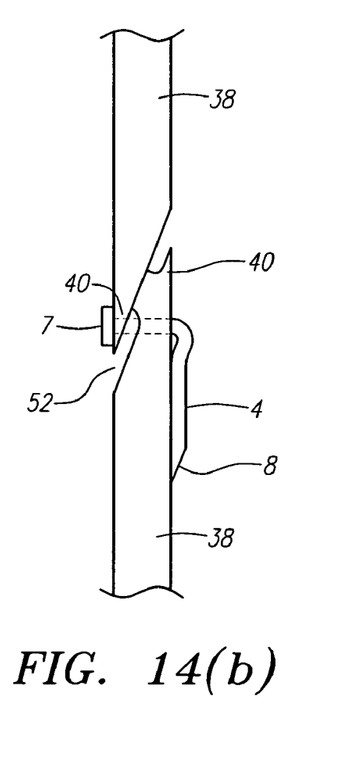

In yet another embodiment of the invention, the clip 2 may have only a single tine 4. In its biased state, the clip 2 is substantially linear, as is shown, for example, in FIG. 12. The clip 2 is deployed by piercing one or more flap(s) of tissue 40 such that a portion of the clip 2 is one side of a septum wall 38 and the remaining portion is on the opposing side of the septum wall 38. Both "halves" of the clip 2 then bend from a stressed state to a relaxed state to close the septal defect. The clip 2 in its relaxed state may take the shape of a "U" or "V" (shown, for example, in FIG. 12), or even an "S" (shown in FIG. 13). FIG. 14 shows yet another embodiment of a clip 2 having a single tine 4. In this embodiment, the retaining end 6 of the clip 2 includes a head 7 that prevents the clip 2 from passing completely through the septum wall 38. In this regard, the clip 2, in its relaxed state, takes the shape of an "L". During deployment of this clip 2, the tine 4 is preferably advanced through the septum wall 38 until the head 7 prevents further advancement of the clip 2.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the spirit and scope of the appended claims.

What is claimed is:

1. A method of closing a septal defect within a patient's heart comprising the steps of:
    advancing an elongate delivery apparatus, adapted to carry a clip apparatus, through the patient's vasculature and into a right atrial chamber of the heart, wherein the atrial septal wall of the heart has a patent foramen ovale characterized by a first tissue flap located mainly in the right atrial chamber and a second tissue flap located mainly in a left atrial chamber, at least a portion of the first tissue flap overlapping at least a portion of the second tissue flap to define a tunnel therebetween; and
    advancing the clip apparatus from the right atrial chamber through the first tissue flap, then into and across the tunnel, then through the second tissue flap and into the left atrial chamber, such that at least part of the clip apparatus resides entirely through the first and second tissue flaps to at least partially close the tunnel.

2. The method of claim 1, wherein advancing the elongate delivery apparatus comprises advancing the distal end of the elongate delivery apparatus into the right atrial chamber until the distal end is disposed adjacent to the patent foramen ovale.

3. The method of claim 2, wherein advancing the clip apparatus comprises advancing a pusher member distally relative to the elongate delivery apparatus to advance the clip apparatus.

4. The method of claim 1, further comprising imaging a portion of the heart.

5. The method of claim 1, further comprising externally imaging the clip apparatus.

6. The method of claim 5, further comprising externally imaging the clip apparatus with ultrasound.

7. The method of claim 5, wherein the clip apparatus comprises a radiopaque marker and wherein externally imaging the clip apparatus comprises externally imaging the radiopaque marker with fluoroscopy.

8. The method of claim 1, wherein advancing the clip apparatus through the vasculature of a subject comprises advancing the clip apparatus through the vasculature while the clip apparatus is in a stressed state.

9. The method of claim 8, comprising allowing the clip apparatus to transition from the stressed, first state to a less stressed, second state.

10. The method of claim 9, wherein the less stressed, second state is a relaxed state with substantially no stress.

11. The method of claim 1, further comprising:
    engaging a first septal surface exposed in the left atrial chamber with a first portion of the clip apparatus; and
    engaging a second septal surface exposed in the right atrial chamber with a second portion of the clip apparatus.

12. The method of claim 11, wherein engaging the first septal surface exposed in the left atrial chamber with the first portion of the clip apparatus comprises allowing the first portion of the clip apparatus to transition from a stressed state to a less stressed state such that the first portion engages the first septal surface.

13. The method of claim 11, wherein the first portion of the clip apparatus comprises a plurality of deflectable members.

14. The method of claim 13, wherein engaging the first septal surface exposed in the left atrial chamber with the first portion of the clip apparatus comprises allowing the plurality of deflectable members to deflect laterally to engage the first septal surface.

15. The method of claim 14, wherein the plurality of deflectable members deflect laterally in directions generally away from each other.

16. The method of claim 11, wherein engaging the second septal surface exposed in the right atrial chamber with the second portion of the clip apparatus comprises allowing the second portion of the clip apparatus to transition from a stressed state to a less stressed state such that the second portion engages the second septal surface.

17. The method of claim 11, wherein the second portion of the clip apparatus comprises a fixed retaining end configured to abut the second septal surface.

18. The method of claim 11, wherein the clip apparatus is monolithic.

19. The method of claim 11, wherein the clip apparatus comprises a plurality of separate segments.

20. The method of claim 11, wherein the first and second septal surfaces are engaged such that the first tissue flap is held in contact with the second tissue flap.

21. The method of claim 20, wherein a part of the clip apparatus that resides within the first flap resides within a piercing in the portion of the first flap that overlaps the second flap.

22. The method of claim 21, wherein a part of the clip apparatus that resides within the second flap resides within a piercing in the portion of the second flap that overlaps the first flap.

23. The method of claim 20, wherein a part of the clip apparatus that resides within the second flap resides within a piercing in the portion of the second flap that overlaps the first flap.

24. The method of claim 23, wherein a part of the clip apparatus that resides within the first flap resides within a piercing in the portion of the first flap that overlaps the second flap.

25. The method of claim 1, wherein the clip apparatus comprises a tip configured to penetrate tissue and wherein advancing the clip apparatus comprises advancing the clip apparatus such that the tip penetrates the first tissue flap.

26. The method of claim 25, wherein advancing the clip apparatus comprises advancing the clip apparatus such that the tip penetrates the second tissue flap.

27. The method of claim 26, wherein the tip is on a tine.

28. The method of claim 26, wherein the clip apparatus comprises a plurality of tips configured to penetrate tissue.

29. The method of claim 26, wherein the tip is located on a first portion of the clip apparatus, the first portion being configured to transition from a first orientation, configured to allow penetration of the septal tissue during advancement of the clip apparatus, to a second orientation configured to engage a first septal surface exposed in the left atrial chamber after penetrating the second tissue flap.

30. The method of claim 29, wherein the tip inflects back towards the atrial septal wall in the second orientation.

31. The method of claim 29, wherein the second orientation has a hook-like configuration.

32. The method of claim 31, wherein the tip inflects back and penetrates the atrial septal wall.

33. The method of claim 29, wherein the second orientation is configured such that at least part of the first portion of the clip apparatus lies substantially flat against the atrial septal wall.

34. The method of claim 33, wherein the second orientation is configured such that the tip lies substantially flat against the septal wall.

35. The method of claim 33, wherein the second orientation is configured such that the majority of the first portion of the clip apparatus lies substantially flat against the septal wall after implantation.

36. The method of claim 29, wherein the first portion is biased to transition from the first orientation to the second orientation.

37. The method of claim 36, wherein the clip apparatus comprises a second portion configured to engage a second septal surface exposed in the right atrial chamber.

38. The method of claim 37, further comprising:
engaging the first septal surface exposed in the left atrial chamber with the first portion of the clip apparatus; and
engaging the second septal surface exposed in the right atrial chamber with the second portion of the clip apparatus.

39. The method of claim 38, wherein the second portion of the clip apparatus comprises a fixed retaining end.

40. The method of claim 38, wherein engaging the second septal surface exposed in the right atrial chamber with the second portion of the clip apparatus comprises allowing the second portion of the clip apparatus to transition from a stressed state to a less stressed state such that the second portion engages the second septal surface.

41. The method of claim 40, further comprising advancing the clip apparatus through a percutaneous entry site near a peripheral vessel to gain access to the vasculature of the subject.

42. The method of claim 41, wherein advancing the elongate delivery apparatus through the vasculature of the subject comprises advancing the elongate delivery apparatus through the inferior vena cava.

43. The method of claim 42, wherein the clip apparatus comprises NITINOL.

44. The method of claim 1, wherein the elongate delivery apparatus comprises a lumen with an open distal end.

45. The method of claim 44, wherein the clip apparatus is slidable within the lumen.

46. The method of claim 45, wherein advancing the clip apparatus comprises advancing the clip apparatus through the distal end of the elongate delivery apparatus with a distal end of an elongate pusher member.

47. The method of claim 46, further comprising advancing the pusher member with an actuator.

48. The method of claim 46, wherein the distal end of the pusher member is configured to engage the clip apparatus.

49. The method of claim 48, wherein the distal end of the pusher member is configured to allow rotational control of the clip apparatus.

50. The method of claim 49, wherein the distal end of the pusher member comprises a notch.

51. The method of claim 49, wherein the clip apparatus is held in a stressed state by the elongate delivery apparatus.

52. The method of claim 51, further comprising allowing at least a first portion of the clip apparatus to transition from the stressed state to a less stressed state after the clip apparatus is advanced from the distal end of the elongate delivery apparatus.

53. The method of claim 52, wherein the first portion of the clip apparatus is a distal portion.

54. The method of claim 53, wherein the first portion of the clip apparatus comprises a tip configured to penetrate tissue.

55. The method of claim 53, wherein advancing the clip apparatus further comprises allowing a second portion of the clip apparatus to transition from a stressed state to a less stressed state after the second portion exits the distal end of the elongate delivery apparatus.

56. The method of claim 48, wherein the inner surface the elongate delivery apparatus is configured to engage the clip apparatus.

57. The method of claim 56, wherein the inner surface of the elongate delivery apparatus comprises a groove.

58. The method of claim 46, wherein the pusher member comprises a radiopaque marker.

59. The method of claim 1, wherein the clip apparatus comprises a radiopaque marker.

60. The method of claim 1, wherein the elongate delivery apparatus comprises a radiopaque marker.

61. The method of claim 1, wherein the clip apparatus comprises stainless steel.

62. The method of claim 1, wherein the clip apparatus comprises NITINOL.

63. The method of claim 1, wherein the clip apparatus comprises a shape memory material.

64. The method of claim 1, wherein the clip apparatus comprises an elastic material.

65. The method of claim 1, wherein the clip apparatus comprises a superelastic material.

66. The method of claim 1, wherein advancing the elongate delivery apparatus through the vasculature of the subject comprises advancing the elongate delivery apparatus through the inferior vena cava.

67. The method of claim 1, wherein advancing the elongate delivery apparatus through the vasculature of the subject comprises advancing the elongate delivery apparatus through the superior vena cava.

68. The method of claim 1, wherein advancing the elongate delivery apparatus through the vasculature of the subject comprises advancing the elongate delivery apparatus through an artery.

69. The method of claim 1, further comprising introducing the elongate delivery apparatus into the vasculature of the patient at a percutaneous entry site to a peripheral vessel, prior to advancing the elongate delivery apparatus.

70. The method of claim 1, comprising orienting the elongate delivery apparatus with respect to the septal wall such as to allow advancement of the clip apparatus into a position suitable for the clip apparatus to close the tunnel.

71. The method of claim 1, further comprising orienting the elongate delivery apparatus perpendicularly with respect to the septal wall prior to advancing the clip apparatus.

72. The method of claim 1, wherein the clip apparatus comprises a central body member that resides through the first and second tissue flaps.

73. The method of claim 1, further comprising:
engaging a first septal surface exposed in the left atrial chamber with a first portion of the clip apparatus; and
engaging a second septal surface exposed in the right atrial chamber with a second portion of the clip apparatus.

74. The method of claim 1, wherein advancing the clip apparatus from the right atrial chamber through the first tissue flap comprises piercing through the first tissue flap with the clip apparatus.

75. The method of claim 1, wherein advancing the clip apparatus comprises piercing the first tissue flap with the clip apparatus.

76. The method of claim 75, wherein the piercing is the sole piercing entirely through the first tissue flap in which the clip apparatus resides.

77. The method of claim 76, wherein the part of the clip apparatus that resides within the piercing is the main body portion of the clip apparatus.

78. The method of claim 1, wherein the clip apparatus resides within a first opening through the first tissue flap and a second opening through the second tissue flap, wherein the first opening is in-line with the second opening.

79. The method of claim 78, further comprising removing the elongate delivery apparatus while leaving the clip apparatus implanted within the first and second openings, wherein the clip apparatus does not reside in any other openings entirely through the first tissue flap or the second tissue flap.

80. The method of claim 1, wherein first tissue flap is the septum secundum and the second tissue flap is the septum primum and the clip apparatus at least partially closes the tunnel by maintaining the left atrial side of the septum secundum in contact with the right atrial side of the septum primum.

81. A method of closing a septal defect within a patient's heart comprising the steps of:
  advancing an elongate delivery apparatus, adapted to carry an implantable device, through the patient's vasculature and into a right atrial chamber of the heart, wherein the atrial septal wall of the heart has a patent foramen ovale characterized by a first tissue flap located mainly in the right atrial chamber and a second tissue flap located mainly in a left atrial chamber, at least a portion of the first tissue flap overlapping at least a portion of the second tissue flap to define a tunnel therebetween; and
  advancing the implantable device from the right atrial chamber through the first tissue flap, then into and across the tunnel, then through the second tissue flap and into the left atrial chamber, such that at least part of the implantable device resides entirely through the first and second tissue flaps to at least partially close the tunnel.

82. The method of claim 81, wherein advancing the elongate delivery apparatus comprises advancing the distal end of the elongate delivery apparatus into the right atrial chamber until the distal end is disposed adjacent to the patent foramen ovale.

83. The method of claim 82, wherein advancing the implantable device comprises advancing a pusher member distally relative to the elongate delivery apparatus to advance the implantable device.

84. The method of claim 81, wherein the implantable device comprises a radiopaque marker, and further comprising externally imaging the radiopaque marker with fluoroscopy.

85. The method of claim 81, wherein advancing the implantable device through the vasculature of a subject comprises advancing the implantable device through the vasculature while the implantable device is in a stressed state.

86. The method of claim 85, comprising allowing the implantable device to transition from the stressed, first state to a less stressed, second state.

87. The method of claim 81, further comprising:
  engaging a first septal surface exposed in the left atrial chamber with a first portion of the implantable device; and
  engaging a second septal surface exposed in the right atrial chamber with a second portion of the implantable device.

88. The method of claim 87, wherein engaging the first septal surface exposed in the left atrial chamber with the first portion of the implantable device comprises allowing the first portion of the implantable device to transition from a stressed state to a less stressed state such that the first portion engages the first septal surface.

89. The method of claim 87, wherein engaging the second septal surface exposed in the right atrial chamber with the second portion of the implantable device comprises allowing the second portion of the implantable device to transition from a stressed state to a less stressed state such that the second portion engages the second septal surface.

90. The method of claim 87, wherein the second portion of the implantable device comprises a fixed retaining end configured to abut the second septal surface.

91. The method of claim 81, wherein advancing the elongate delivery apparatus through the vasculature of the subject comprises advancing the elongate delivery apparatus through the inferior vena cava.

92. The method of claim 81, wherein advancing the elongate delivery apparatus through the vasculature of the subject comprises advancing the elongate delivery apparatus through the superior vena cava.

93. The method of claim 81, further comprising introducing the elongate delivery apparatus into the vasculature of the patient at a percutaneous entry site to a peripheral vessel, prior to advancing the elongate delivery apparatus.

94. The method of claim 81, wherein advancing the implantable device from the right atrial chamber through the first tissue flap comprises piercing through the first tissue flap with the implantable device.

95. The method of claim 81, wherein advancing the implantable device comprises piercing the first tissue flap with the implantable device.

96. The method of claim 95, wherein the piercing is the sole piercing entirely through the first tissue flap in which the implantable device resides.

97. The method of claim 96, wherein the part of the implantable device that resides within the piercing is a main body portion of the implantable device.

98. The method of claim 81, wherein the implantable device resides within a first opening through the first tissue flap and a second opening through the second tissue flap, wherein the first opening is in-line with the second opening.

99. The method of claim 98, further comprising removing the elongate delivery apparatus while leaving the implantable device implanted within the first and second openings, wherein the implantable device does not reside in any other openings entirely through the first tissue flap or the second tissue flap.

100. The method of claim 81, wherein first tissue flap is the septum secundum and the second tissue flap is the septum primum and the implantable device at least partially closes the tunnel by maintaining the left atrial side of the septum secundum in contact with the right atrial side of the septum primum.

* * * * *